(12) United States Patent
Palasis et al.

(10) Patent No.: US 7,892,205 B2
(45) Date of Patent: Feb. 22, 2011

(54) DEVICE AND METHOD FOR DELIVERING MICRONIZED THERAPEUTIC AGENTS IN THE BODY

(75) Inventors: Maria Palasis, Wellesley, MA (US);
Wendy Naimark, Cambridge, MA (US);
Toby Freyman, Waltham, MA (US);
Samuel Epstein, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1056 days.

(21) Appl. No.: 10/455,298

(22) Filed: Jun. 6, 2003

(65) Prior Publication Data

US 2004/0249359 A1 Dec. 9, 2004

(51) Int. Cl.
*A61M 37/00* (2006.01)
(52) U.S. Cl. .................. 604/147; 604/149; 604/246
(58) Field of Classification Search ............. 604/256, 604/35, 140–142, 147, 23–26, 537, 93.01, 604/118, 119, 131, 146, 149, 246–248, 523; 433/83
See application file for complete search history.

(56) References Cited

U.S. PATENT DOCUMENTS

| | | | | |
|---|---|---|---|---|
| 1,223,243 A | * | 4/1917 | Bessesen | ............. 604/183 |
| 2,946,332 A | | 7/1960 | Sacks | |
| 3,630,196 A | * | 12/1971 | Bird et al. | ............. 128/200.18 |
| 3,952,742 A | | 4/1976 | Taylor | |
| 4,620,847 A | | 11/1986 | Shishov et al. | |
| 4,945,050 A | | 7/1990 | Sanford et al. | |
| 5,204,253 A | * | 4/1993 | Sanford et al. | ............. 435/459 |
| 5,478,744 A | | 12/1995 | Sanford et al. | |
| 5,843,022 A | * | 12/1998 | Willard et al. | ............. 604/30 |
| 5,964,223 A | | 10/1999 | Baran | |
| 6,079,413 A | | 6/2000 | Baran | |
| 6,194,389 B1 | | 2/2001 | Johnston | |
| 6,328,714 B1 | | 12/2001 | Bellhouse et al. | |
| 6,436,709 B1 | | 8/2002 | Lin et al. | |
| 6,475,181 B1 | | 11/2002 | Potter et al. | |

(Continued)

FOREIGN PATENT DOCUMENTS

DE 298 06 361 U1 9/1998

(Continued)

OTHER PUBLICATIONS http://www.lehmanlaw.com/newsletter/pharma/20010926.htm.

(Continued)

*Primary Examiner*—Nicholas D Lucchesi
*Assistant Examiner*—Theodore J Stigell
(74) *Attorney, Agent, or Firm*—Vidas, Arrett & Steinkraus P.A.

(57) ABSTRACT

The present invention provides a catheter and catheter assembly for delivering micronized therapeutic agents to a target site in the body and, in particular, to a target site in the heart. The micronized therapeutic agents are delivered in aerosol form or dry powder form. The present invention also provides a method of delivering micronized therapeutic agents to a target site in the body by placing the therapeutic agents in a catheter, positioning the catheter in the target site, and exposing the therapeutic agents to an energizing mechanism sufficient to create supersonic flow to carry the therapeutic agents from a stationary state in the catheter to a mobile state towards the target site.

6 Claims, 3 Drawing Sheets

U.S. PATENT DOCUMENTS

| | | | |
|---|---|---|---|
| 6,511,477 | B2 | 1/2003 | Altman et al. |
| 6,514,482 | B1 | 2/2003 | Bartus et al. |
| 2001/0038859 | A1 | 11/2001 | Maskiewicz et al. |
| 2002/0004641 | A1 | 1/2002 | Bellhouse et al. |

FOREIGN PATENT DOCUMENTS

| | | |
|---|---|---|
| GB | 607 237 | 8/1848 |
| GB | 607237 | 8/1948 |
| GB | 1 436 028 | 5/1976 |
| JP | 08-038607 | 2/1996 |
| JP | 2003-515383 T | 5/2003 |
| WO | 01/39682 A1 | 6/2001 |
| WO | WO 01/56637 | 8/2001 |
| WO | WO 02/056948 A1 | 7/2002 |

OTHER PUBLICATIONS http://www.algorz.com/pwdtech.html.
http://www.tribuneindia.com/1999/99nov03/health.htm.
http://www.eiffeltechnologies.com.au/pda.htm.
http://www.powderject.com/media/press_releases/180302.htm.
http://www.bioportfolio.com/news/algorx_1.htm.
http://www.powderject.com/media/press_releases/090997_3.htm.
http://www.the-scientist.com/yr1997/august/tools1_970818.html.
PCT International Search Report dated Nov. 22, 2004, Scimed Life Systems, Inc., No. PCT/US2004/014956.

\* cited by examiner

DEVICE AND METHOD FOR DELIVERING MICRONIZED THERAPEUTIC AGENTS IN THE BODY

FIELD OF THE INVENTION

The present invention relates to the delivery of micronized therapeutic agents to a target site in the body through the use of a catheter and catheter assembly.

BACKGROUND OF THE INVENTION

Therapeutic agents are often delivered directly to target sites of diseased tissue in various contemporary medical procedures. This direct delivery has proven to be an advantageous approach when treating numerous medical conditions. Advantages of this procedure are that only the target site may be exposed to the therapeutic and a controlled dose of therapeutic may be directly delivered to the target tissue.

Despite the advantages of direct delivery, one pronounced disadvantage is that the low viscosity of the therapeutic may result in the therapeutic being ejected or squeezed back through its point of entry in the target tissue. This problem is exacerbated in situations where the therapeutic is injected into an actively contracting tissue such as the myocardium of the heart. In such a case, the low-viscosity therapeutic may be ejected or squeezed out through its point of entry by the repeated expansion and contraction of the heart muscle. This unintended and unwanted leakage can result in an unascertainable dosage of the therapeutic being ultimately received by the target site and arbitrary and unwanted interaction between leaked therapeutic and neighboring tissue and muscle.

As such, it is advantageous for a therapeutic to have a high solid content to retard its ejection from a target site. A therapeutic with a high solid to fluid ratio, however, may resist passage through a delivery lumen thereby necessitating the use of a solvent to provide an operative balance of solids to fluids. In these cases, however, the solvent employed may be toxic in relation to the target site or incompatible with the therapeutic.

There is, therefore, a need in the art for a method and apparatus that provides efficient direct delivery of a therapeutic to a target site while allowing for easy passage through a delivery lumen of a delivery device.

SUMMARY OF THE INVENTION

One embodiment of the present invention provides a method of delivering therapeutic agents to a target site in the body comprising providing a catheter having a distal end and a proximal end, placing therapeutic agents in the catheter, positioning the distal end of the catheter at the target site, exposing the therapeutic agents to an energizing mechanism to move the therapeutic agents from a stationary state to a mobile state, micronizing the therapeutic agents to form micronized therapeutic agents, and ejecting the micronized therapeutic agents from the distal end of the catheter to the target site.

Another embodiment of the present invention provides a method of delivering therapeutic agents to a target site in the heart comprising providing a catheter having a distal end and a proximal end, positioning the distal end of the catheter at the target site of the heart, and delivering micronized therapeutic agents through the catheter to the target site of the heart.

Another embodiment of the present invention provides a catheter assembly comprising a catheter having a lumen extending therethrough, a proximal end, and a distal end including a nozzle. The catheter includes a therapeutic agent reservoir, a pressurization chamber located between the therapeutic agent reservoir and the nozzle, a loading valve positioned between the therapeutic agent reservoir and the pressurization chamber, and an injection valve positioned between the pressurization chamber and the nozzle. The catheter assembly further comprises a pressurized gas delivery tube having a first end and a second end, the first end connected to a pressurized gas source and the second end in fluid communication with the pressurization chamber of the catheter.

Yet another embodiment of the present invention provides a catheter assembly comprising a catheter having a lumen extending therethrough, a proximal end, and a distal end including a nozzle. The catheter includes a therapeutic agent reservoir, a vacuum chamber located between the therapeutic agent reservoir and the nozzle, and a loading valve positioned between the therapeutic agent reservoir and the vacuum chamber. The catheter assembly further includes a vacuum delivery tube having a first end and a second end, the first end connected to a vacuum source and the second end in fluid communication with the vacuum chamber of the catheter.

Another embodiment of the present invention provides a catheter comprising a shaft having a lumen extending therethrough and a rotor located within the lumen of the shaft, the rotor configured to accept micronized therapeutic agents.

DETAILED DESCRIPTION OF THE INVENTION

The present invention is generally directed to a device and method of delivering micronized therapeutic agents to a target site of the body by positioning a catheter at a target site and delivering micronized therapeutic agents through the catheter to the target site. The micronized therapeutic agents are delivered to the target site of the body by any energizing mechanism sufficient to create a high speed flow, such as a supersonic flow, to carry the micronized therapeutic agents from a stationary state in the catheter to a mobile state. Non-limiting examples of such energizing mechanisms include pressurized gas, vacuum, mechanical force, electric potential gradient, and centripetal force.

Figure 1:
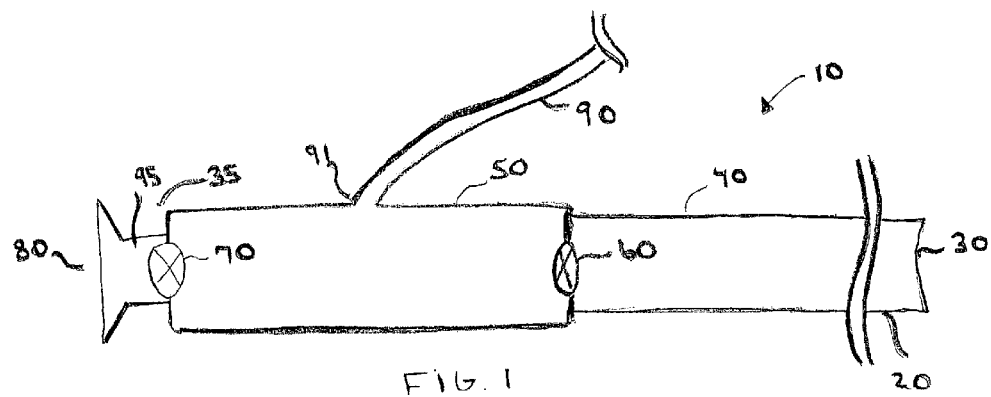
FIG. 1 depicts an embodiment of a catheter assembly according to the present invention.
Figure 2:
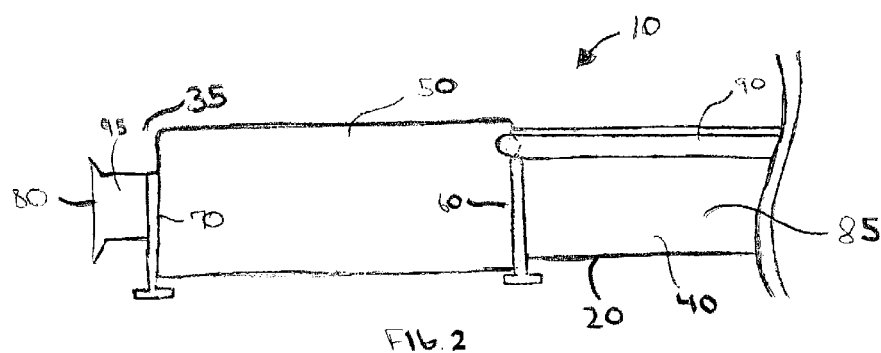
FIG. 2 depicts an alternative embodiment of a catheter assembly according to the present invention.

Referring to FIGS. 1 and 2, one embodiment of the present invention, where the energizing mechanism is pressurized gas, provides a catheter assembly 10 comprising a catheter 20 having a lumen 85 extending therethrough, a proximal end 30, and a distal end 35 including a nozzle 80 having a channel 95 extending therethrough. In this embodiment of the present invention, catheter 20 has at least two compartments: a therapeutic agent reservoir 40 and a pressurization chamber 50, the latter of which is located between therapeutic agent reservoir 40 and nozzle 80. Catheter 20 further includes a loading valve 60 positioned between therapeutic agent reservoir 40 and pressurization chamber 50 and an injection valve 70 positioned between pressurization chamber 50 and nozzle 80. Preferably, therapeutic agent reservoir 40, pressurization chamber 50, loading valve 60, and injection valve 70 are located closer to distal end 35 of catheter 20 than proximal end 30. Catheter assembly 10 further comprises a pressurized gas delivery tube 90 having a first end (not shown) and a second end 91. First end is connected to a pressurized gas source (not shown) and second end 91 is in fluid communication with pressurization chamber 50 of catheter 20. Delivery tube 90 may be located outside of catheter 20, as illustrated in FIG. 1, or inside lumen 85 of catheter 20, as illustrated in FIG. 2.

In an exemplary use of catheter assembly 10 illustrated in FIG. 1 or 2, therapeutic agents are loaded in the therapeutic agent reservoir 40, catheter 20 is inserted into the body, and nozzle 80 is placed in the target site. Loading valve 60 is opened and the therapeutic agents in therapeutic agent reservoir 40 are introduced into pressurization chamber 50. Loading valve 60 is then closed and pressurized gas is delivered to pressurization chamber 50 via delivery tube 90. Once a sufficient amount of pressure accumulates in pressurization chamber 50, injection valve 70 is opened and the therapeutic agents pass through nozzle 80 and enter the target site.

Although the pressurized gas that is used to create the high pressure in pressurization chamber 50 varies, it is preferably maintained at a pressure of about 1000 pounds per square inch. (PSI). Preferably, the gas is helium, because of its light weight and characteristic of having a high speed of expansion. Other preferred gases include nitrogen, air, or hydrogen.

The therapeutic agents may be micronized prior to loading in therapeutic agent reservoir 40 or may be micronized prior to exit from catheter 20. For example, the therapeutic agents loaded in catheter 20 may have a reduced particle size such as a micronic particle size or the therapeutic agents may have any particle size and are atomized by a narrow channel 95 of nozzle 80 prior to exit from catheter 20.

In an alternative embodiment, therapeutic agent reservoir 40 and pressurization chamber 50 are not compartments of catheter 20, but are components that are inserted into catheter 20. For example, pressurization chamber 50 could comprise a micro-cylinder filled with gas at a specific pressure and having a gas cylinder tip, and therapeutic agent reservoir 40 could comprise a cassette or package filled with a predetermined amount of micronized therapeutic agents. To operate this device according to the present invention, the catheter is positioned at the target site and an actuation pin contacts and breaks the gas cylinder tip of the micro-cylinder. Breaking of the gas cylinder tip releases the compressed gas inside the micro-cylinder, which bursts the drug cassette or package and delivers the therapeutic agent to the target site.

Catheter assembly 10 may also include a gauge to measure the pressure in the pressurization chamber 50 to determine when a threshold pressure has been obtained and therefore to determine when to terminate delivery of the pressurized gas from the pressurized gas source.

Figure 3:
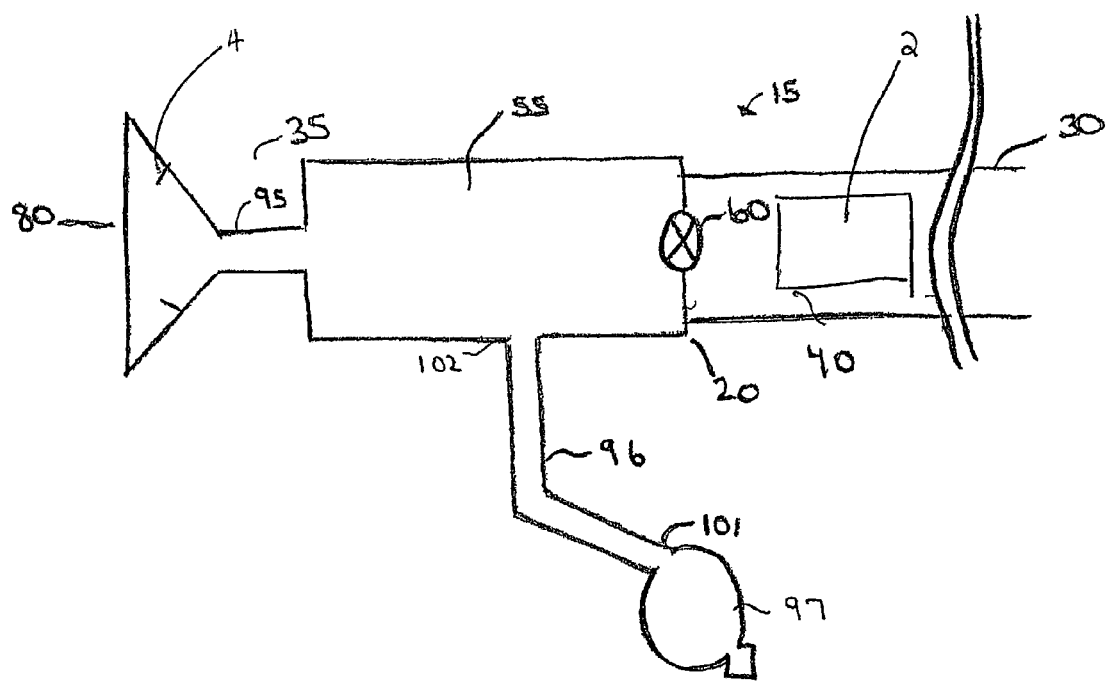
FIG. 3 depicts an embodiment of a catheter assembly according to the present invention.

Referring to FIG. 3, another embodiment of the present invention, where the energizing mechanism is a vacuum source, provides a catheter assembly 15 comprising a catheter 20 having a lumen 85 extending therethrough, a proximal end 30, and a distal end 35 including a nozzle 80 having a channel 95 extending therethrough. In this embodiment of the present invention, catheter 20 also has at least two compartments: a therapeutic agent reservoir 40 and a vacuum chamber 55, the latter of which is located between therapeutic agent reservoir 40 and nozzle 80. Catheter 20 further includes a loading valve 60 positioned between therapeutic agent reservoir 40 and vacuum chamber 55. Preferably, therapeutic agent reservoir 40, vacuum chamber 55 and loading valve 60 are located closer to distal end 35 of catheter 20 than proximal end 30. Catheter assembly 10 further comprises a vacuum delivery tube 96 having a first end 101 and a second end 102 wherein first end 101 is connected to a vacuum source 97 and second end 102 is in fluid communication with vacuum chamber 55. Delivery tube 96 may be located outside of catheter 20, as illustrated in FIG. 3, or inside lumen 85 of catheter 20.

In an exemplary use of this embodiment, therapeutic agents are loaded in catheter 20, catheter 20 is inserted into the body, and nozzle 80 is pressed against the target site to create a sealed environment between catheter 20 and the target site. Vacuum source 97 is activated and a vacuum is drawn through vacuum delivery tube 96 into vacuum chamber 55 to reduce the pressure inside vacuum chamber in relation to the pressure in therapeutic agent reservoir 40. Loading valve 60 is then opened and therapeutic agents are drawn into vacuum chamber 55 and pass through channel 95 of nozzle 80 into the target site. Once again, the therapeutic agents may be micronized prior to loading into catheter 20 or may be micronized prior to exit from catheter 20. For example, the therapeutic agents loaded in catheter 20 may have a reduced particle size or the therapeutic agents may have any particle size and are atomized by a narrow channel 95 of nozzle 80 prior to exit from catheter 20. Although the embodiment depicted in FIG. 3 illustrates a vacuum source 97 being used as the energizing mechanism to move the micronized therapeutic agent from a stationary state to a mobile state, a vacuum source may also be used in conjunction with other energizing mechanisms described herein or contemplated by the present invention to maximize the speed of the energizing mechanism, minimize the frictional deacceleration of the micronized therapeutic agents and/or to reduce the air pressure inside catheter 20.

Figure 4:
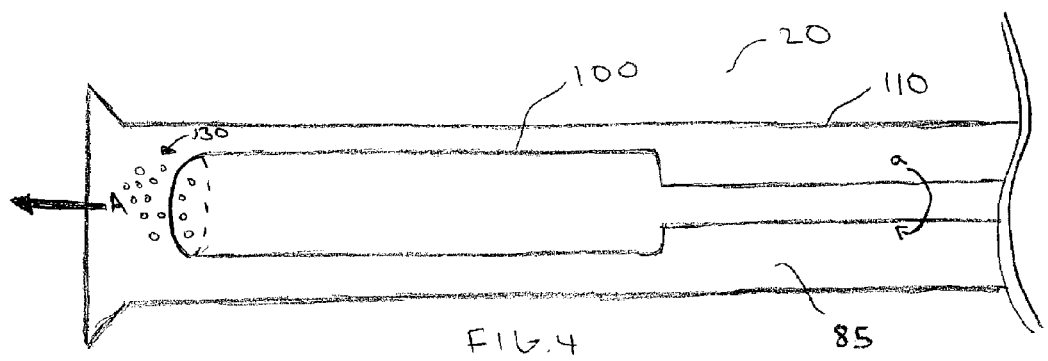
FIG. 4 depicts an embodiment of a catheter according to the present invention.
Figure 5:
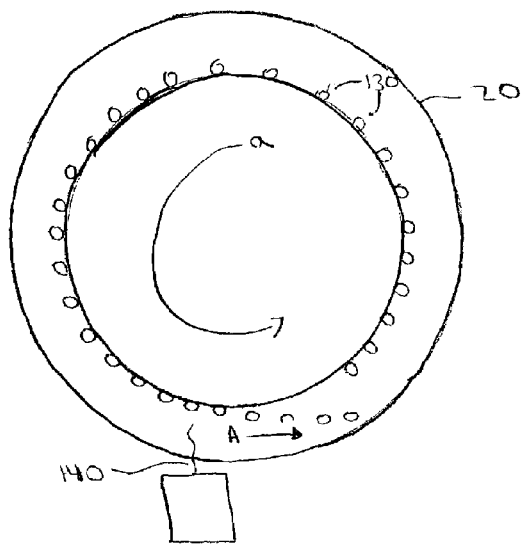
FIG. 5 depicts an alternative embodiment of a catheter according to the present invention.

Referring to FIGS. 4 and 5, another embodiment of the present invention, where the energizing mechanism is centripetal force, provides a catheter 20 comprising a shaft 110 having a lumen 85 extending therethrough and a rotor 100 located within lumen 85. Rotor 100 is configured to accept micronized therapeutic agents 130. As illustrated in FIG. 4, rotor 100 may be in the form of a cylinder which can hold micronized therapeutic agents 130, or as illustrated in FIG. 5, rotor 100 may be in the form of a disk to which micronized therapeutic agents 130 can adhere. Other suitable configurations of rotor 100 will be readily appreciated by one skilled in the art and therefore such other configurations are within the scope of the present invention. In order to release micronized therapeutic agents 130 from rotor 100 to the target site, rotor 100 is rotated at a high speed as indicated by arrow a and then the rotation is terminated causing micronized therapeutic agents 130 to eject from the rotor 100 in a direction tangential to the axis of the rotor's rotation as indicated by arrow A. The velocity of the micronized therapeutic agents 130 is controlled by the circular velocity of rotor 100.

Referring specifically to FIG. 5, in embodiments where rotor 100 is a disk, and micronized therapeutic agents 130 are bound to the outer edge of rotor 100, the micronized therapeutic agents may be control released by focusing an energy beam 140, such as a laser beam, at a specific point on the outer edge of rotor 100. The energy of the beam 140 is adapted to and causes release of the micronized therapeutic agents 130 from the surface of the rotor 100, causing such micronized therapeutic agents to continue at a predetermined velocity in a straight line tangential to the point of release and thus to be directed towards the target site. The micronized therapeutic agents 130 may be attached to rotor 100, for example, by electrostatic forces, by their natural sticky nature, or by the evaporation of ethanol or another solvent in which the micronized therapeutic agents have been suspended. The energy beam is selected to impart energy of a nature and in an amount sufficient to overcome the forces of adhesion existing between the micronized therapeutic agents 130 and the rotor and to release the micronized therapeutic agents 130 without adversely affecting the micronized therapeutic agents essential properties.

Figure 6:
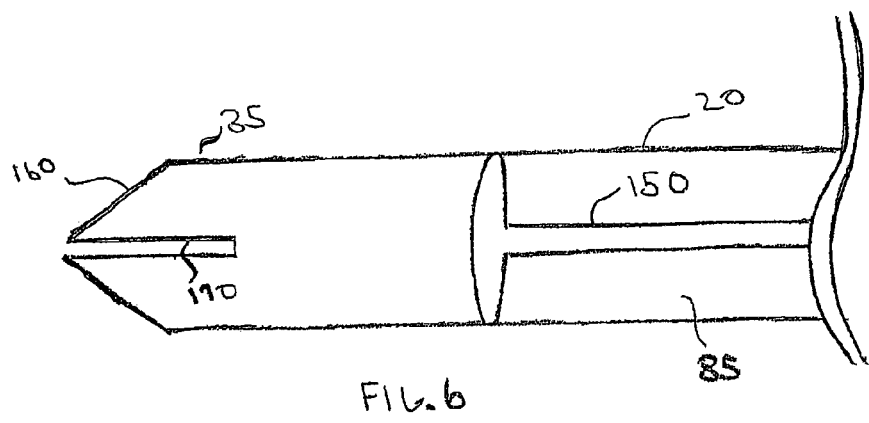
FIG. 6 depicts an embodiment of a catheter according to the present invention.

Referring to FIG. 6, another embodiment of the present invention, where the energizing mechanism is a mechanical mechanism, provides a catheter 20 having a lumen 85 extending therethrough, and having a distal end 35 including a needle 160 having a channel 170 extending therethrough. A mechanical member, such as a plunger 150, is located within lumen 185 and is configured to exert pressure on therapeutic agents located within lumen 85 to eject the therapeutic agents in micronized form through channel 170 of needle 160 into the target site. Although the mechanical member is depicted as a plunger in FIG. 5, any other mechanical member capable of exerting pressure on the therapeutic agents is also within the scope of the present invention. The therapeutic agents may be micronized prior to loading in catheter 20 or may be micronized prior to exit from catheter 20. For example, the therapeutic agents loaded in catheter 20 may have a reduced particle size or the therapeutic agents may have any particle size and are atomized by a narrow channel 170 of needle 160 prior to exit from catheter 20.

Another embodiment of the present invention, where the energizing mechanism is an electric potential gradient, provides a catheter assembly comprising a catheter having a lumen extending therethrough, a proximal end including an active electrode, and a distal end including a counter electrode and a nozzle. The catheter assembly also includes a source of electrical energy such as a battery or pulse generator to which the active electrode and counter electrode are connected. A charged therapeutic agent is delivered through the active electrode and migrates along the electric potential gradient formed by the circuit of the counter electrode and the active electrode through the nozzle of the catheter to the target site. For example, if the therapeutic agent to be delivered is positively charged, then an anode will be the active electrode and a cathode will be the counter electrode to complete the electrical circuit. If the therapeutic agent to be delivered is negatively charged, then a cathode will serve as the active electrode and an anode will be the counter electrode.

Figures 7A, 7B:
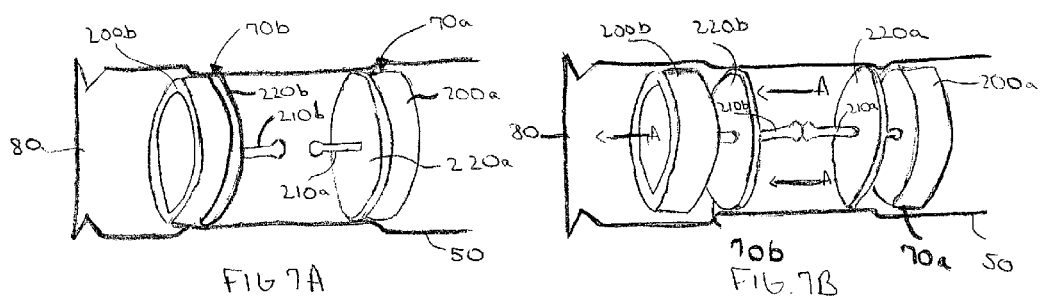
FIG. 7 depicts a component of a catheter according to the present invention.

With respect to particular details of the present invention, in embodiments including an injection valve 70 and/or a loading valve 60, these valves may be any type of valve such as, for example, a plug valve, a ball valve, a butterfly valve, or a gate valve. Preferably, injection valve 70 comprises a valve stem 200a, 200b as illustrated in FIG. 7 that is actuated by exertion of force thereupon. In particular, injection valve 70 includes a valve stem 200a, 200b, which is a hollow member, an axially elongated pin 210a, 210b, and a seal 220a, 220b that covers valve stem 200a, 200b. Although FIG. 7 depicts two valve stems 200a, 200b, only at least one valve stem is contemplated by this preferred embodiment of the present invention. As illustrated in FIG. 7A, seals 220 cover respective valve stems 200a, 200b in a resting position thereof (i.e. when no force is exerted upon valve stems 200a, 200b) so that no therapeutic agents are released from pressurization chamber 50 into channel 95 of nozzle 80. As illustrated in FIG. 7B, in an actuated position of valve stems 200a, 200b, when force is exerted on valve stem 200a, pin 210a depresses pin 210b such that valve stems 200a, 200b are released from contact with their respective seals 220a, 220b and the aerosol of therapeutic agents are released from pressurization chamber 50 and pass around pins 210a and 210b, through valve stems 200a, 200b and into nozzle 80 as indicated by arrows A. The force exerted on valve stem 200a can originate, for example, from a pre-set amount of pressure released from a pressurization source through pressurized gas delivery tube 90 into pressurization chamber 50, as described in relation to FIGS. 1 and 2 or by a pre-set amount of pressure created by vacuum source 97 through vacuum delivery tube 96 into vacuum chamber 55 as described in relation to FIG. 3, or by mechanical force created by a mechanical member as described in relation to FIG. 6.

With respect to characteristics of the micronized therapeutic agents according to the present invention, the therapeutic agents may be micronized prior to entry into a catheter according to the present invention or may be micronized prior to exit from the catheter. With respect to being micronized prior to entry into a catheter, the therapeutic agents may be micronized by any means known in the art such as micronization or microencapsulation by destructive or constructive methods. Non-limiting examples of destructive methods include crushing and grinding, granulation, and spray formation. Non-limiting examples of constructive methods include evaporation/condensation, physico-chemical methods, crystallization, and vapor condensation. The micronized therapeutic agents are delivered to the target site at a high velocity in either solid dry powder form or aerosol form. Preferably the micronized therapeutic agents are delivered at velocities of at least about 150 m/s or more, and more preferably at velocities of about 250-300 m/s or greater.

With respect to micronizing the therapeutic agents prior to exit from a catheter according to the present invention, the catheter may define or include a baffle 4 or narrow passage near the distal end thereof to atomize the therapeutic agents prior to exit from the catheter.

Notwithstanding how the therapeutic agents are micronized, the therapeutic agents may be directly inserted into a catheter (or, specifically, a therapeutic agent reservoir) according to the present invention or may be inserted into a cassette or cylinder which is, in turn, inserted into a catheter. In the latter embodiment, the cassette 2 or cylinder would burst or rupture upon the application of the energizing mechanism to the cassette or cylinder thereby releasing the therapeutic agent to the target site.

With respect to the micronized "therapeutic agent" such an agent may be one or more "therapeutic agents" or "drugs." The terms "therapeutic agents" and "drugs" are used interchangeably herein and include pharmaceutically active compounds, nucleic acids with and without carrier vectors such as lipids, compacting agents (such as histones), virus (such as adenovirus, adenoassociated virus, retrovirus, lentivirus and α-virus), polymers, hyaluronic acid, proteins, cells and the like, with or without targeting sequences.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); anti-restenosis agents such as cladribine; antioxidants such as probucol and retinoic acid; angiogenic and anti-angiogenic agents and factors; anti-proliferative agents such as enoxaprin, angiopeptin, rapamycin, angiopeptin, monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, acetylsalicylic acid, and mesalamine; calcium entry blockers such as verapamil, diltiazem and nifedipine; antineoplastic/antiproliferative/antimitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vasoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the insertion site and any modifications to such cells are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor alpha and beta, platelet-derived endothelial growth factor, platelet-derived growth factor, tumor necrosis factor alpha, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

To provide controlled release of the therapeutic agents used in the present invention, the therapeutic agents may be microencapsulated with polymers to form a polymeric material/therapeutic agent matrix. Preferably, the polymer is characterized by all of the following: biocompatibility, controlled release characteristics, biodegradation capabilities, transfection capabilities, deterrence to the flocculation of the therapeutic agents, and sufficient density if utilized in aerosol form. Such a polymeric material/therapeutic agent matrix can be formed by admixing a therapeutic agent with a liquid polymer, in the absence of a solvent, to form a liquid polymer/therapeutic agent mixture. Curing of the mixture typically occurs in situ. To facilitate curing, a cross-linking or curing agent may be added to the mixture prior to application thereof. Addition of the cross-linking or curing agent to the polymer/therapeutic agent liquid mixture should not occur too far in advance of the application of the mixture in order to avoid over-curing of the mixture prior to application thereof. Curing may also occur in situ by exposing the polymer/therapeutic agent mixture, after application to the luminal surface, to radiation such as ultraviolet radiation or laser light, heat, or by contact with metabolic fluids such as water at the site where the mixture has been applied to the luminal surface. In coating systems employed in conjunction with the present invention, the polymeric material may be either bioabsorbable or biostable. Any of the polymers described herein that may be formulated as a liquid may be used to form the polymer/therapeutic agent mixture. When delivered into the target site, the therapeutic agent is released from the polymer as it slowly dissolves into the aqueous bodily fluids and diffuses out of the polymer.

The polymer used in the present invention to encapsulate the therapeutic agent is preferably capable of absorbing a substantial amount of drug solution and may be hydrophilic or hydrophobic, and may be selected from the group consisting of polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers and copolymers. Encapsulation from polymer dispersions such as polyurethane dispersions (BAYHDROL®, etc.) and acrylic latex dispersions are also within the scope of the present invention. The polymer may be a protein polymer, fibrin, collagen and derivatives thereof, polysaccharides such as celluloses, starches, dextrans, alginates and derivatives of these polysaccharides, an extracellular matrix component, hyaluronic acid, or another biologic agent or a suitable mixture of any of these, for example. In one embodiment of the invention, the preferred polymer is polyacrylic acid, available as HYDROPLUS® (Boston Scientific Corporation, Natick, Mass.), and described in U.S. Pat. No. 5,091,205, the disclosure of which is hereby incorporated herein by reference.

The methods and devices of the present invention may be implanted or otherwise utilized in any body lumina and organ such as the coronary vasculature, esophagus, trachea, colon, biliary tract, urinary tract, prostrate, brain, lung, liver, heart, skeletal muscle, kidney, bladder, intestines, stomach, pancreas, ovary, cartilage, eye, bone, and the like.

The micronized therapeutic agents can be used, for example, in any application for treating, preventing, or otherwise affecting the course of a disease or tissue or organ dysfunction. For example, the methods and devices of the present invention can by used to induce or inhibit angiogenesis, as desired, to present or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

The foregoing description has been set forth merely to illustrate the invention is not intended as being limiting. Each of the disclosed embodiments may be considered individually or in combination with other embodiments of the invention, other variations, and other aspects of the invention. Modifications of the disclosed embodiments incorporating the spirit and substance of the invention may occur to persons skilled in the art. Therefore, the present invention should be construed to include everything within the scope of the appended claims and equivalents thereof.

We claim:

1. A catheter assembly for insertion into a body lumen, the catheter assembly comprising:
   a catheter having a lumen extending therethrough, a proximal end, and a distal end including a nozzle, the catheter including
   a therapeutic agent reservoir defined by the lumen;
   a vacuum chamber defined by the lumen located between the therapeutic agent reservoir and the nozzle;
   a loading valve positioned between the therapeutic agent reservoir and the vacuum chamber within the lumen; and
   a vacuum delivery tube having a first end and a second end, the first end connected to a vacuum source and the second end in fluid communication with the vacuum chamber of the catheter.

2. The catheter assembly of claim 1, further comprising a cassette comprising a therapeutic agent insertable in the therapeutic agent reservoir.

3. The catheter assembly of claim 1, further comprises a baffle near the distal end of the catheter to atomize a therapeutic agent from the therapeutic agent reservoir prior to exit from the catheter.

4. The catheter assembly of claim 1, wherein the nozzle of the catheter defines a narrow passage to atomize a therapeutic agent from the therapeutic agent reservoir prior to exit from the catheter.

5. The catheter assembly of claim 1, wherein the loading valve is manually actuatable.

6. The catheter assembly of claim 1, wherein the vacuum chamber, in its entirety, is located distal of the therapeutic agent reservoir.

* * * * *